United States Patent
Silver et al.

(10) Patent No.: US 10,378,972 B2
(45) Date of Patent: Aug. 13, 2019

(54) PHYSIOLOGICAL INPUT TO DETERMINE VALIDITY OF DATA

(71) Applicant: ZOLL MEDICAL CORPORATION, Chelmsford, MA (US)

(72) Inventors: Annemarie Elizabeth Silver, Bedford, MA (US); Gary A. Freeman, Waltham, MA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 602 days.

(21) Appl. No.: 14/538,588

(22) Filed: Nov. 11, 2014

(65) Prior Publication Data
US 2015/0134297 A1 May 14, 2015

Related U.S. Application Data

(60) Provisional application No. 61/903,298, filed on Nov. 12, 2013.

(51) Int. Cl.
| | |
|---|---|
| *G01K 17/00* | (2006.01) |
| *A61B 5/00* | (2006.01) |
| *G16H 40/63* | (2018.01) |
| *A61B 5/1455* | (2006.01) |
| *G01K 13/00* | (2006.01) |
| *A61B 5/01* | (2006.01) |

(52) U.S. Cl.
CPC .......... *G01K 17/00* (2013.01); *A61B 5/14551* (2013.01); *A61B 5/7221* (2013.01); *G01K 13/002* (2013.01); *G16H 40/63* (2018.01); *A61B 5/01* (2013.01); *A61B 2560/0242* (2013.01)

(58) Field of Classification Search
CPC .. G01K 17/00; G01K 13/002; G06F 19/3406; A61B 5/01; A61B 5/7221; A61B 5/14551; A61B 2560/0242
USPC ........................................................ 702/182
See application file for complete search history.

(56) References Cited

U.S. PATENT DOCUMENTS

| 7,532,919 B2 | 5/2009 | Soyemi et al. |
| 2004/0125996 A1* | 7/2004 | Eddowes et al. .... A61B 5/0059 382/128 |

(Continued)

OTHER PUBLICATIONS

Binzoni, et al., "Haemodynamic Responses to Temperature Changes of Human Skeletal Muscle Studied by Laser-Doppler Flowmetry," Physiol. Meas. 33 (2012), pp. 1181-1197, 17 pages.

*Primary Examiner* — Dzung Tran
(74) *Attorney, Agent, or Firm* — Wilmer Cutler Pickering Hale and Dorr LLP (57) ABSTRACT

Systems and methods for determining validity of physiological data according to an embodiment of the present invention include a patient sensor configured to acquire patient data from a patient, wherein the patient data is physiological; and an environmental sensor configured to acquire environmental data related to validity of the patient data, wherein a value of the environmental data has a clinical effect on the validity of the patient data but not on performance of the environmental sensor; a control/monitoring system, wherein the control/monitoring system is configured to determine whether the environmental data satisfies one or more conditions indicative of the validity of the patient data and to flag the patient data that is invalid based on the determination.

19 Claims, 6 Drawing Sheets

(56) References Cited

U.S. PATENT DOCUMENTS

| | | | | |
|---|---|---|---|---|
| 2004/0154550 A1* | 8/2004 | McQuilkin | A61B 5/415 | 119/174 |
| 2006/0122473 A1* | 6/2006 | Kill et al. | G01J 5/04 | 600/300 |
| 2007/0055171 A1* | 3/2007 | Fraden | G01K 1/165 | 600/549 |
| 2007/0106172 A1* | 5/2007 | Abreu | A61B 5/0002 | 600/549 |
| 2008/0214949 A1* | 9/2008 | Stivoric et al. | A61B 5/0008 | 600/549 |
| 2009/0105605 A1* | 4/2009 | Abreu | A61B 5/0008 | 600/549 |
| 2013/0267863 A1* | 10/2013 | Orr | A61B 5/0836 | 600/532 |
| 2015/0094914 A1* | 4/2015 | Abreu | B60H 1/00742 | 701/41 |

\* cited by examiner

PHYSIOLOGICAL INPUT TO DETERMINE VALIDITY OF DATA

CROSS-REFERENCE TO RELATED APPLICATION

This application claims the benefit of U.S. Provisional Patent Application Ser. No. 61/903,298, filed on Nov. 12, 2013, which is incorporated by reference herein in its entirety for all purposes.

TECHNICAL FIELD

Embodiments of the present invention relate generally to determination of validity of patient data, and more specifically to use of physical inputs to determine validity of patient data.

BACKGROUND

Often, the collection of physiological data can be influenced by environmental conditions such as temperature. For example, muscle blood flow may change with varying temperature. See Binzoni, Tiziano et al., Haemodynamic Responses to Temperature Changes of Human Skeletal Muscle Studied by Laser-Doppler Flowmetry. Physiol. Meas. 33 (2012), pp. 1181-1197. Clinicians may fail to realize, particularly in emergency situations, that the physiological data they are recording and/or seeing is being impacted and/or invalidated by the presence of environmental factors.

SUMMARY

Systems for determining validity of physiological data according to an embodiment of the present invention include a patient sensor configured to acquire patient data from a patient, wherein the patient data is physiological; and an environmental sensor configured to acquire environmental data related to validity of the patient data, wherein a value of the environmental data has a clinical effect on the validity of the patient data but not on performance of the environmental sensor; a control/monitoring system, wherein the control/monitoring system is configured to determine whether the environmental data satisfies one or more conditions indicative of the validity of the patient data and to flag or identify the patient data that is invalid based on the determination.

Methods for flagging or identifying validity of physiological data according to an embodiment of the present invention include acquiring patient data from a patient with a patient sensor, wherein the patient data is physiological; and acquiring environmental data related to validity of the patient data with an environmental sensor, wherein a value of the environmental data has a clinical effect on the patient and on the validity of the patient data but not on performance of the environmental sensor; with a control/monitoring system, determining whether the environmental data satisfies one or more conditions indicative of the validity of the patient data and flagging the patient data that is invalid based on the determination.

A method for modifying physiological data to compensate for environmental conditions influencing a patient according to an embodiment of the present invention includes acquiring patient data from a patient with a patient sensor, wherein the patient data is physiological; and acquiring environmental data related to validity of the patient data with an environmental sensor, wherein a value of the environmental data has a clinical effect on the patient and/or on the validity of the patient data but not on performance of the environmental sensor; with a control/monitoring system, modifying the patient data to compensate for the environmental data based on an experimental correlation of the patient data and the environmental data.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
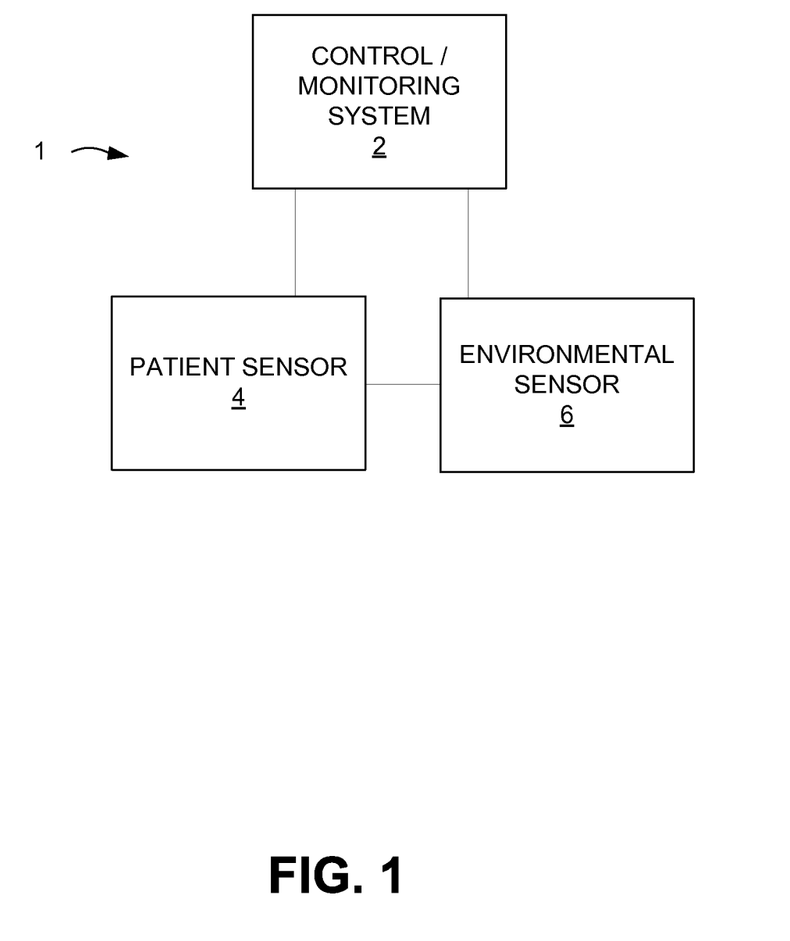
FIG. 1 illustrates a system for identifying environmental influence on a physiological sensor, according to embodiments of the present invention.

FIG. 1 illustrates a system 1 for identifying environmental influence on a physiological sensor, according to embodiments of the present invention. System 1 includes a patient sensor 4 and an environmental sensor 6, according to embodiments of the present invention. Patient sensor 4 is communicably coupled to a control/monitoring system 2, which may receive data from the patient sensor 4 and/or store and/or display such data. The control/monitoring system 2 may be any of a number of different devices, including but not limited to a defibrillator, a portable defibrillator, or a patient monitor. The control/monitoring system 2 may also be communicably coupled to an environmental sensor 6, either directly and/or via the patient sensor 4, according to embodiments of the present invention.

According to embodiments of the present invention, patient sensor 4 may be of a type influenced by environmental factors. For example, the patient sensor 4 may be affected by temperature and/or movement. According to other embodiments of the present invention, the patient sensor 4 may obtain data regarding a physiological condition of a patient, but the validity and/or accuracy of such physiological data may be affected by environmental conditions to which the patient is exposed, for example temperature and/or movement of the patient. According to some embodiments of the present invention, the environmental sensor 6 conveys information about one or more environmental conditions to the control/monitoring system 2 in order to assist the control/monitoring system, and ultimately an end user, in determining whether patient data acquired by the patient sensor 4 is valid and/or accurate in the presence of the one or more environmental conditions. While FIG. 1 illustrates one patient sensor 4 and one environmental sensor 6, one of ordinary skill in the art, based on the present disclosure, will understand that multiple patient sensors and/or environmental sensors, either similar to or different from sensors 4, 6, may be communicably coupled to control/monitoring system 2 and used in a similar manner, according to embodiments of the present invention.

Some embodiments of the present invention include various steps, some of which may be performed by hardware components or may be embodied in machine-executable instructions. These machine-executable instructions may be used to cause a general-purpose or a special-purpose processor programmed with the instructions to perform the steps. Alternatively, the steps may be performed by a combination of hardware, software, and/or firmware. In addition, some embodiments of the present invention may be performed or implemented, at least in part (e.g., one or more modules), on one or more computer systems, mainframes (e.g., IBM mainframes such as the IBM zSeries, Unisys ClearPath Mainframes, HP Integrity NonStop servers, NEC Express series, and others), or client-server type systems. In addition, specific hardware aspects of embodiments of the present invention may incorporate one or more of these systems, or portions thereof.

Figure 2:
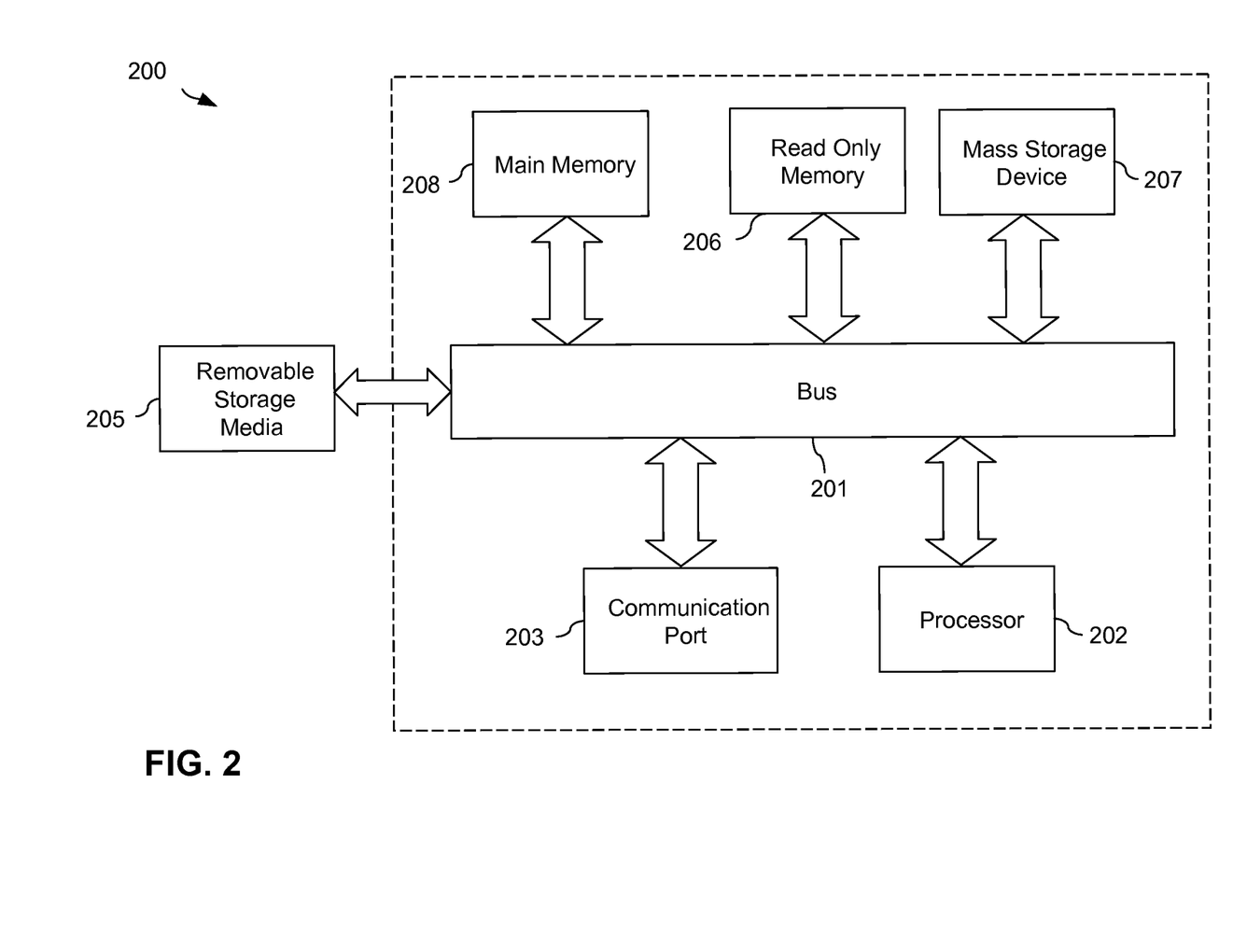
FIG. 2 illustrates a computer system, according to embodiments of the present invention.

As such, FIG. 2 is an example of a computer system 200 with which embodiments of the present invention may be utilized. According to the present example, the computer system includes a bus 201, at least one processor 202, at least one communication port 203, a main memory 204, a removable storage media 205, a read only memory 206, and a mass storage 207. According to some embodiments of the present invention, the control/monitoring system 2 is or includes one or more computer systems 200.

Processor(s) 202 can be any known processor, such as, but not limited to, an Intel® Itanium® or Itanium 2® processor(s), or AMD® Opteron® or Athlon MP® processor(s), or Motorola® lines of processors. Communication port(s) 203 can be any of an RS-232 port for use with a modem based dialup connection, a 10/100 Ethernet port, or a Gigabit port using copper or fiber, for example. Communication port(s) 203 may be chosen depending on a network such a Local Area Network (LAN), Wide Area Network (WAN), or any network to which the computer system 200 connects. Main memory 204 can be Random Access Memory (RAM), or any other dynamic storage device(s) commonly known to one of ordinary skill in the art. Read only memory 206 can be any static storage device(s) such as Programmable Read Only Memory (PROM) chips for storing static information such as instructions for processor 202, for example.

Mass storage 207 can be used to store information and instructions. For example, hard disks such as the Adaptec® family of SCSI drives, an optical disc, an array of disks such as RAID (e.g. the Adaptec family of RAID drives), or any other mass storage devices may be used, for example. Bus 201 communicably couples processor(s) 202 with the other memory, storage and communication blocks. Bus 201 can be a PCI/PCI-X or SCSI based system bus depending on the storage devices used, for example. Removable storage media 205 can be any kind of external hard-drives, floppy drives, flash drives, IOMEGA® Zip Drives, Compact Disc-Read Only Memory (CD-ROM), Compact Disc-Re-Writable (CD-RW), or Digital Video Disk-Read Only Memory (DVD-ROM), for example. The components described above are meant to exemplify some types of possibilities. In no way should the aforementioned examples limit the scope of the invention, as they are only exemplary embodiments.

During normal environmental conditions, patient sensor 4 operates normally and the data values generated by patient sensor 4 are received, stored, displayed, and/or otherwise employed by the control/monitoring system 2. During environmental conditions which fall within a condition range or ranges which are known to affect the sensor 4 or the validity or accuracy of sensor 4, the control/monitoring system 2 is configured to identify the patient sensor 4 data values associated with such environmental sensor 6 data readings. Such patient sensor 4 data may be flagged, for example flagged as it is recorded or stored, and/or such patient sensor 4 data may be ignored or dropped if system 2 determines that the data was acquired under environmental conditions falling outside of validity ranges. If control/monitoring system 2 displays the patient sensor 4 data or a summary or derivation thereof, the control/monitoring system 2 may be further configured to also display a visual indication of the environmental sensor 6 conditions under which the patient sensor 4 data was acquired. For example, a red dot or warning bar may be displayed by control/monitoring system 2 when displaying patient sensor 4 data acquired while the environmental sensor 6 sensed a certain condition in an environmental factor, according to embodiments of the present invention.

Figure 3:
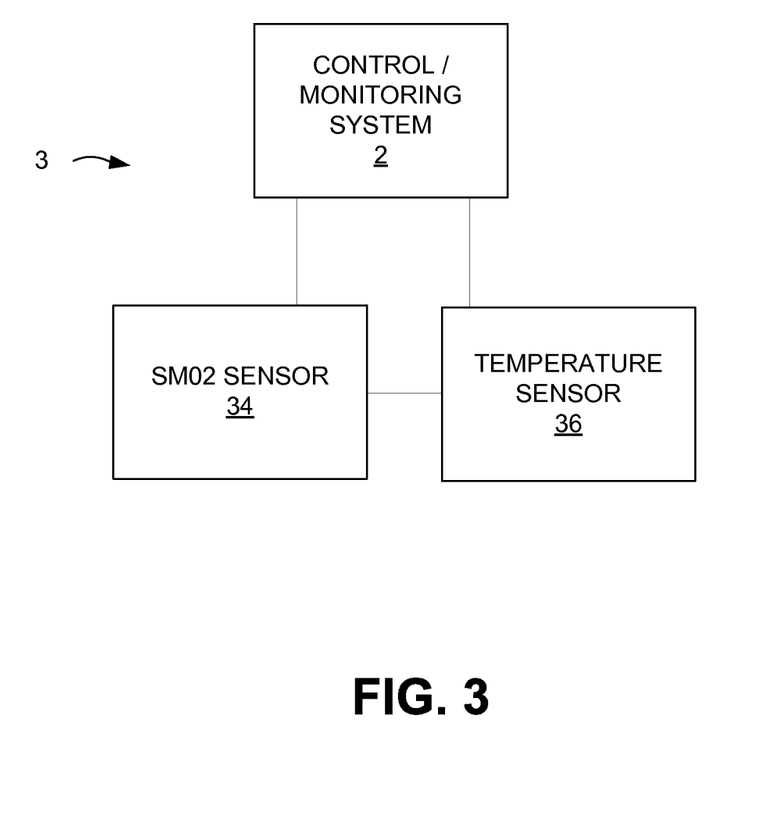
FIG. 3 illustrates a system for identifying environmental influence on a physiological sensor, according to embodiments of the present invention.

FIG. 3 illustrates a system 3 for identifying environmental influence on a physiological sensor, according to embodiments of the present invention. System 3 is similar to system 1, except the patient sensor 4 is a muscle oxygen saturation (SmO2) sensor 34, and the environmental sensor 6 is a temperature sensor 36, according to embodiments of the present invention. According to some embodiments of the present invention, the SmO2 sensor 34 includes additional sensors and/or sensing capabilities, for example pH sensors. According to some embodiments of the present invention, SmO2 sensor 34 is a Multi-Parameter Mobile CareGuide™ oximeter sensor available from Reflectance Medical Inc. According to some embodiments of the present invention, the muscle oxygen saturation sensor 34 may be a tissue oxygen saturation sensor as described in U.S. Pat. No. 7,532,919, issued on May 12, 2009.

In some cases, tissue oxygenation sensors such as sensor 34 may not function optimally in cold temperatures because the cold temperatures may cause blood to be shunted away from a patient's periphery to a patient's core. In such situations, the control/monitoring system 2 will not be able to determine whether a particular patient's low muscle oxygen saturation reading from sensor 34 is being caused by the cold or by other physiological factors or conditions. In some embodiments of the present invention, there are some temperatures below which the data acquired by SmO2 sensor 34 becomes potentially clinically invalid, and should not be relied upon by the caregiver. In other cases, tissue oxygenation sensors such as sensor 34 may not function optimally in warmer temperatures. For example, if the skin heats up when the sensor 34 is turned on, this could increase SmO2 and blood flow. This could, for example, make the sensor 34 readings unstable initially. Such data could be adjusted, as described herein, so that such variability does not become visible to the user, according to embodiments of the present invention.

The temperature sensor 36 may be a temperature probe and/or thermocouple, and may be placed so as to acquire a temperature reading from the patient's skin (for example at or near the site on the patient's skin where the SmO2 sensor 34 is placed), the ambient temperature where the patient is being monitored or treated, and/or internally to the patient. The temperature sensor 36 may, in some embodiments, be configured to monitor and/or derive a core body temperature of the patient being treated for use by the control/monitoring system 2 in assessing the validity of the sensor 34 data. As described above, more than one temperature sensor 36 may be used, for example for redundancy and/or averaging and/or acquiring different readings from different locations on, in, or off the patient.

Figure 4:
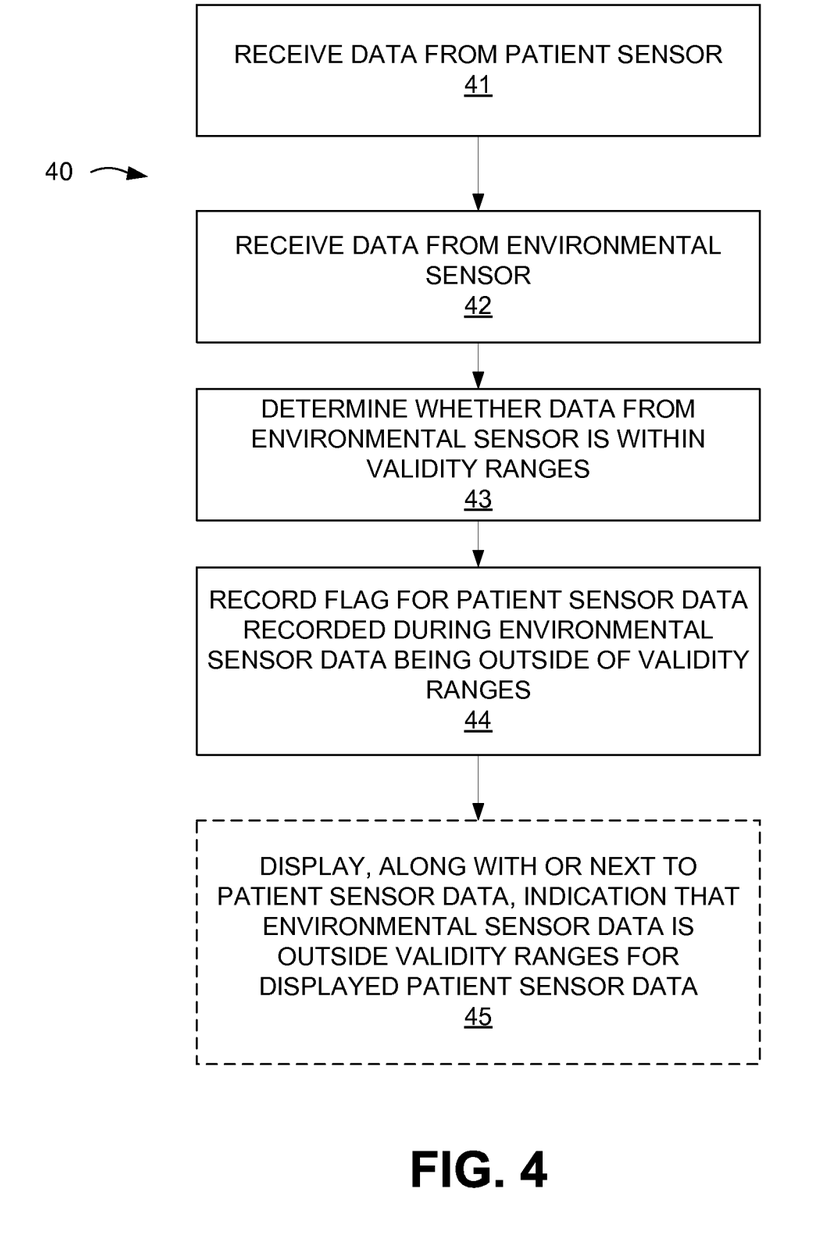
FIG. 4 depicts a flow chart illustrating a method for flagging patient sensor data which may have been acquired under environmental conditions outside of a certain validity range, according to embodiments of the present invention.

FIG. 4 depicts a flow chart 40 illustrating a method for flagging patient sensor data which may have been acquired under environmental conditions outside of a certain validity range, according to embodiments of the present invention. Data is received from the patient sensor 4, for example by control/monitoring system 2 (block 41), according to embodiments of the present invention. Data is also received from environmental sensor 6, for example by control/monitoring system 2 (block 42), according to embodiments of the present invention. The control/monitoring system 2 may then determine whether the data from the environmental sensor 6 is within certain validity ranges (block 43), and record a flag for patient sensor data recorded while environmental sensor data is outside of the validity range or ranges (block 44). This flag may be in any form, tangible or intangible, such that the flag is connected to the particular data from the patient sensor 4 and indicates whether such data is inside and/or outside of a validity range based on the environmental condition sensed by environmental sensor 6. Optionally, if the data from the patient sensor 4 is displayed, or a subset or summary or derivation of such data is displayed, a further visual indicator may be displayed with or next to the patient sensor 4 data to indicate that the environmental sensor 6 data is outside of the validity range (block 45), according to embodiments of the present invention. The functionality illustrated in FIGS. 4 and 5 may be performed, for example, by a control/monitoring system 2, for example a computer system 200, according to embodiments of the present invention.

Figure 5:
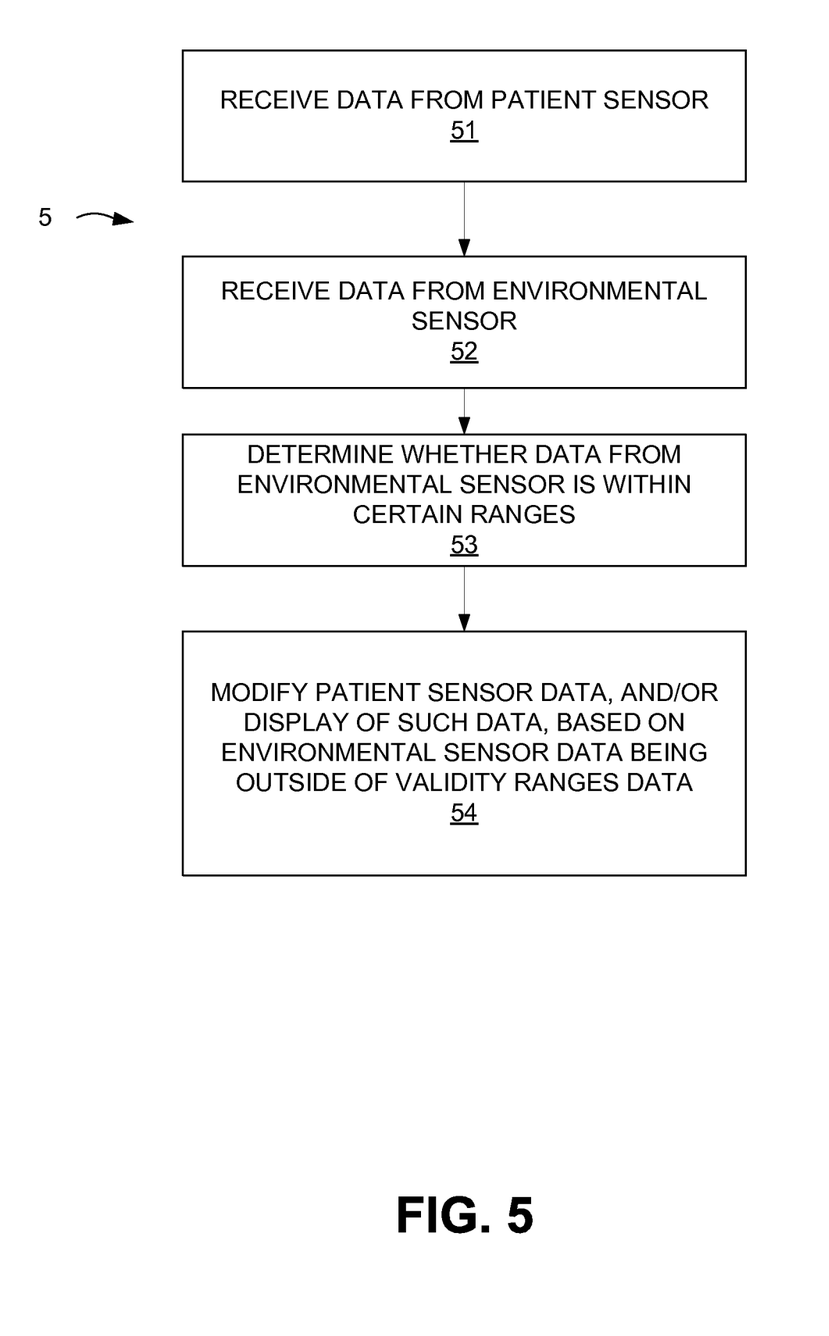
FIG. 5 depicts a flow chart illustrating a method for modifying patient sensor data or display based on environmental data, according to embodiments of the present invention.

FIG. 5 depicts a flow chart 5 illustrating a method for modifying patient sensor data or display based on environmental data, according to embodiments of the present invention. Similar to method 40, method 5 involves receiving data from the patient sensor (block 51), receiving data from the environmental sensor (block 52), and determining whether data from the environmental sensor 6 is within certain ranges (block 53). Instead of flagging whether the data from patient sensor 4 is invalid based on the environmental conditions, as illustrated in FIG. 4, the control/monitoring system 2 may be configured to input data from the environmental sensor 6 into an algorithm or correlation that modifies or adjusts the data from the patient sensor 4 to compensate for the effects of the environmental condition (block 54). For example, for any given patient sensor 4, such as for example SmO2 sensor 34, one or more experiments may be performed to determine a correlation of the particular sensed environmental condition or conditions to the clinical accuracy of the patient sensor 4. For example, for a given SmO2 sensor, experiments may be performed to determine a correlation between temperature (whether it be skin, ambient, or internal/core) and the patient's muscle oxygen saturation. Such experiments may be performed over a wide range of patients or subjects, and/or over a wide range of conditions for the same subject. Such data may be analyzed to determine a correlation between the temperature and the muscle oxygen saturation data, and such correlation may be used by the control/monitoring system 2 to compensate for the effect of temperature on the SmO2 sensor data. Methods such as logistic regression can be utilized to generate a logistic equation that correct for the effects of the temperature measurements.

Figure 6:
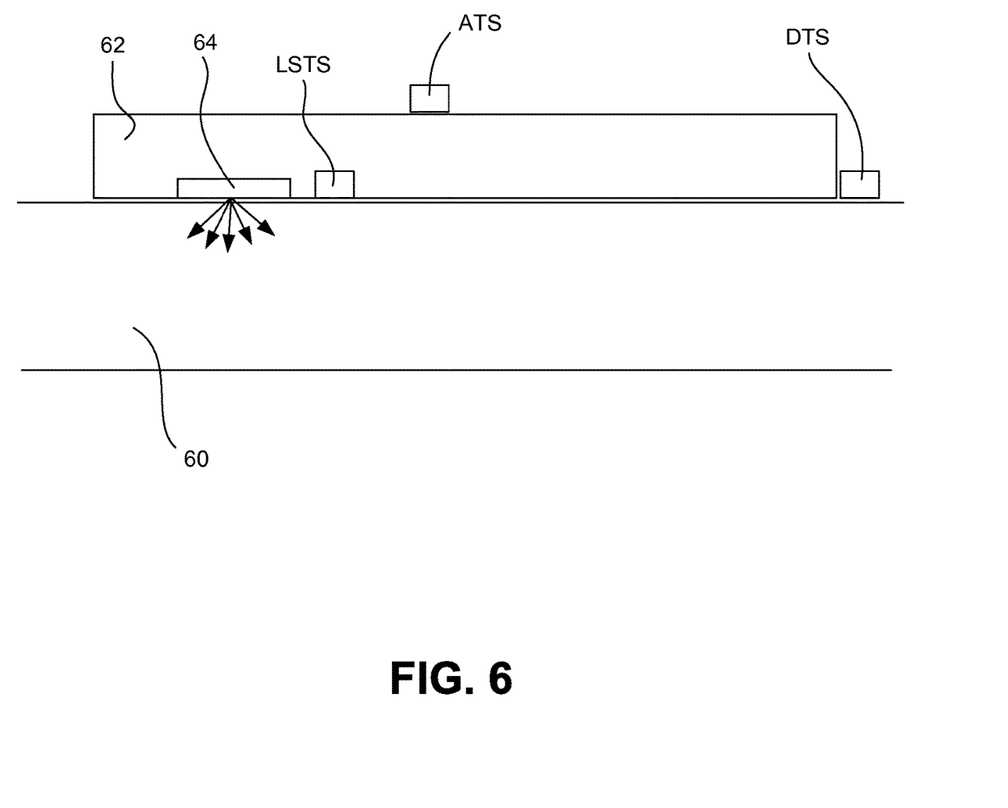
FIG. 6 illustrates a side elevation partial cross-sectional view of a muscle oxygen saturation sensor applied to a patient's skin, according to embodiments of the present invention.

Multiple temperature sensors may be used to calculate a better estimate of the reactivity of the patient to ambient temperature. In one example, as shown in FIG. 6, there may be a temperature sensor that measures surface skin temperature directly beneath the light source 64 from the SmO2 sensor 62 which may cause localized heating of the skin 60 ("Light Source Temperature Sensor", LSTS). A separate sensor may face outward on the sensor and measure ambient temperature ("Ambient Temperature Sensor", ATS), and a third sensor may measure skin temperature at the distal end of the SmO2 sensor, away from the light source and potential for localized heating of the skin ("Distal Temperature Sensor", DTS). By comparing the readings from the LSTS and the DTS, a measure of localized heating can be calculated and input to the logistic equation to correct the sensor measurement. The temperature difference between the ATS and DTS will provide some indication of the reactivity of the particular patient to ambient temperature and also input into the logistic equation or other mathematical method for correcting for temperature effects.

Other environmental conditions may be sensed with respect to other kinds of patient sensors, according to embodiments of the present invention. For example, in peripheral blood oxygen saturation (SpO2) measurement, the sensor 4 may be an SpO2 sensor, and the sensor 6 may be a temperature sensor, similar to the system 3 described with respect to FIG. 3, according to embodiments of the present invention.

According to some embodiments of the present invention, the determination of whether to characterize data acquired by the patient sensor 4 is automated based on validity ranges provided to or stored by control/monitoring system 2. Such validity range data may be stored in memories 205, 207, and/or 208, according to embodiments of the present invention. Instead of a range, other comparisons or inequality equations may be applied to the environmental sensor 6 data to determine the presence of certain conditions.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:
1. A system for determining validity of oxygen saturation data, the system comprising:
   an oxygenation sensor configured to acquire oxygen saturation data from tissue of a patient;
   a temperature sensor configured to be positioned at a location to acquire temperature data from the tissue of the patient while the oxygenation sensor acquires the oxygen saturation data from the tissue of the patient; and a monitoring system comprising a memory storing instructions, and a processor that, when executing the instructions, causes the monitoring system to:

determine whether the temperature data satisfies one or more pre-stored conditions indicative of the validity of the oxygen saturation data and to identify the oxygen saturation data as invalid if the temperature data does not satisfy the one or more pre-stored conditions; and display the oxygen saturation data if the temperature data satisfies the one or more pre-stored conditions.

2. The system of claim 1, wherein the monitoring system is further configured to display an indication of the invalidity of the oxygen saturation data if the temperature data does not satisfy the one or more pre-stored conditions.

3. The system of claim 1, wherein the oxygenation sensor is a muscle oxygen saturation sensor configured to acquire muscle oxygen saturation data from the patient, and wherein the monitoring system is configured to identify the muscle oxygen saturation data as invalid if the temperature data indicates the temperature of the tissue of the patient is below a predetermined threshold.

4. The system of claim 3, wherein the temperature sensor is positioned to sense a skin temperature of the patient.

5. The system of claim 3, wherein the temperature sensor is positioned to sense an internal temperature of the patient.

6. The system of claim 3, wherein the temperature sensor is configured to determine a core temperature of the patient.

7. The system of claim 1, wherein the oxygenation sensor is a muscle oxygen saturation sensor configured to acquire muscle oxygen saturation data from the tissue of the patient, and wherein the monitoring system is configured to identify the muscle oxygen saturation data as invalid if the temperature data indicates the temperature of the tissue of the patient is above a predetermined threshold.

8. The system of claim 7, wherein the temperature sensor is positioned to sense a skin temperature of the patient.

9. The system of claim 7, wherein the temperature sensor is positioned to sense an internal temperature of the patient.

10. The system of claim 7, wherein the temperature sensor is configured to determine a core temperature of the patient.

11. A computer-implemented method for flagging validity of oxygen saturation data, the method comprising:

acquiring oxygen saturation data from tissue of a patient with an oxygenation sensor;

acquiring temperature data from the tissue of the patient with a temperature sensor positioned at a location to acquire the temperature data while the acquiring the oxygen saturation data with an oxygenation sensor; and with a monitoring system:

determining, by a processor in the monitoring system, whether the temperature data satisfies one or more pre-stored conditions indicative of the validity of the oxygen saturation data;

flagging, by the processor in the monitoring system, the oxygen saturation data as invalid if the temperature data does not satisfy the one or more pre-stored conditions; and displaying the-oxygen saturation data if the temperature data satisfies the one or more pre-stored conditions.

12. The method of claim 11, further comprising displaying an indication of the validity of the oxygen saturation data.

13. The method of claim 11, wherein the oxygenation sensor is a muscle oxygen saturation sensor configured to acquire muscle oxygen saturation data from the tissue of the patient, the method further comprising flagging the muscle oxygen saturation data as invalid if the temperature data indicates the temperature of the tissue of the patient is below a predetermined threshold.

14. The method of claim 13, further comprising positioning the temperature sensor to sense a skin temperature of the patient.

15. The method of claim 13, further comprising positioning the temperature sensor to sense an internal temperature of the patient.

16. The method of claim 13, further comprising using the temperature sensor to determine a core temperature of the patient.

17. A computer-implemented method for modifying oxygen saturation data to compensate for temperature, the method comprising:

acquiring oxygen saturation data from tissue of a patient with an oxygenation sensor;

acquiring temperature data from the tissue of the patient with a temperature sensor positioned at a location to acquire the temperature data while the acquiring the oxygen saturation data with an oxygenation sensor; and with a monitoring system:

determining, by a processor in the monitoring system, whether the temperature data satisfies one or more pre-stored conditions indicative of the validity of the oxygen saturation data;

modifying the oxygen saturation data to compensate for the temperature data based on a pre-stored correlation of the oxygen saturation data and the temperature data, when it is determined that the temperature data does not satisfy the one or more pre-stored conditions indicative of the validity of the oxygen saturation data; and displaying the modified oxygen saturation data.

18. The system of claim 1, wherein the monitoring system is configured to display the oxygen saturation data only if the temperature data satisfies the one or more pre-stored conditions.

19. The method of claim 11, wherein the oxygen saturation data is displayed only if the temperature data satisfies the one or more pre-stored conditions.

* * * * *